(12) United States Patent
Goldsmith

(10) Patent No.: US 8,602,032 B2
(45) Date of Patent: Dec. 10, 2013

(54) PATIENT POSITIONING SYSTEM

(76) Inventor: Gary Paul Goldsmith, Dallas, TX (US)

( * ) Notice: Subject to any disclaimer, the term of this patent is extended or adjusted under 35 U.S.C. 154(b) by 284 days.

(21) Appl. No.: 13/091,346

(22) Filed: Apr. 21, 2011

(65) Prior Publication Data

US 2012/0266899 A1  Oct. 25, 2012

(51) Int. Cl.
*A61F 5/37* (2006.01)

(52) U.S. Cl.
USPC .......................................................... 128/876

(58) Field of Classification Search
USPC ............ 128/869, 876, 878, 879, 881; 602/20, 602/62; 5/621, 623, 646, 647; 2/908, 910, 2/912, 917
See application file for complete search history.

(56) References Cited

U.S. PATENT DOCUMENTS

| | | | | | |
|---|---|---|---|---|---|
| 2,679,842 | A | * | 6/1954 | Brill | 128/878 |
| 3,297,026 | A | * | 1/1967 | Van Pelt | 128/878 |
| 3,474,781 | A | * | 10/1969 | Gaylord, Jr. | 128/876 |
| 3,878,844 | A | * | 4/1975 | Tobias | 128/876 |
| 3,939,829 | A | * | 2/1976 | Spann | 128/878 |
| 4,377,284 | A | * | 3/1983 | Okerlin | 473/450 |
| 4,481,942 | A | * | 11/1984 | Duncan | 128/878 |
| 4,515,155 | A | * | 5/1985 | Wagemann | 128/874 |
| 5,263,496 | A | * | 11/1993 | Cherniak | 5/630 |
| 5,309,926 | A | * | 5/1994 | Mayton | 128/869 |
| 5,515,869 | A | * | 5/1996 | Powell et al. | 5/628 |
| 5,651,375 | A | * | 7/1997 | Cunningham | 128/869 |
| 6,000,402 | A | * | 12/1999 | Able | 128/869 |
| 6,132,393 | A | * | 10/2000 | Lundberg | 602/19 |
| 6,545,193 | B1 | * | 4/2003 | Morgenstern | 602/41 |
| 6,936,018 | B2 | * | 8/2005 | Chalek | 602/2 |
| 2005/0091749 | A1 | * | 5/2005 | Humbles | 5/646 |
| 2005/0121041 | A1 | * | 6/2005 | Barnitz | 128/879 |

\* cited by examiner

*Primary Examiner* — Justine R Yu
*Assistant Examiner* — Raymond E Harris (57) ABSTRACT

A method, system, and apparatus for positioning a patient. A set of arm positioning sleeves is provided. Each arm positioning sleeve in the set of arm positioning sleeves is wrapped around a portion of an arm of a user lying on an operating table. One end of each body strap in a set of body straps is connected to a set of rails of the operating table. A set of body strap fasteners is provided that includes a set of hook-and-loop fastener material strips attached to an inner surface of each body strap. An opposing set of hook-and-loop material strips is attached to a portion of an outer surface of each arm positioning sleeve. The set of opposing hook-and-loop material strips on the set of arm positioning sleeves fastens to the set of hook-and-loop fastener material strips on the set of body straps to secure each arm of the user lying on the operating table in a desired position.

19 Claims, 7 Drawing Sheets

PATIENT POSITIONING SYSTEM

BACKGROUND OF THE INVENTION

1. Field

The present invention is related generally to positioning a patient. More particularly, the present invention is directed to a method, apparatus, and system for positioning the extremities of a patient for a medical procedure.

2. Background

Medical procedures may frequently require that a patient be positioned and secured in a particular position. For example, a procedure may necessitate placing a patient on an operating table in either a supine or prone position with arms secured at the sides of the operating table. A supine position refers to the patient lying flat on their back. A prone position refers to the patient lying face down. An operating table may also be referred to as an operating bed or an operating surface.

During a medical procedure, the arms of a patient are typically secured to their sides to prevent movement of the arms and pressure on the arms while the patient is under anesthesia. The arms of the patient are typically secured to their sides using sheets, tape, or a sled.

For example, current methods generally involve using sheets wrapped around a patient's arms and tucked under the patient's body. However, the sheets frequently loosen. Sleds of metal or hard plastic may be used to hold the arm or other limb against the patient's side. However, sleds are large and have to be placed under the patient's torso. This increases the risk of pressure damage to the skin. Sleds may also frequently slip out of position, negating their intended function.

In general, application of these currently available techniques is also cumbersome and time consuming. Likewise, these currently available techniques frequently result in sub-optimal positioning and support of the arms and shoulders.

SUMMARY

An illustrative embodiment provides a system for patient positioning. A set of arm positioning sleeves is provided. Each arm positioning sleeve in the set of arm positioning sleeves is wrapped around a portion of an arm of a user lying on an operating table. One end of each body strap in a set of body straps is affixed to the operating table at one end. A set of body strap fasteners is provided that includes a set of hook-and-loop fastener material strips attached to an inner surface of each body strap. A set of opposing hook-and-loop material strips is attached to a portion of an outer surface of each arm positioning sleeve. The set of opposing hook-and-loop material strips on the portion of the outer surface of each positioning sleeve fastens to the set of hook-and-loop fastener material strips on the set of body straps to secure each arm of the user lying on the operating table in a desired position.

Another illustrative embodiment provides an arm positioning sleeve. The arm positioning sleeve includes an inner surface partially in contact with an arm of a user when in use and an outer surface. The arm positioning sleeve has a first end opposite to a second end. The arm positioning sleeve includes a first longitudinal side opposite to a second longitudinal side. An arm sleeve fastener includes a set of hook-and-loop fastener material strips on the inner surface along the first longitudinal side. The arm sleeve fastener also includes a set of opposing hook-and-loop material strips on the outer surface. The arm positioning sleeve is wrapped around a portion of the arm of the user. The set of hook-and-loop fastener material strips on the inner surface of the arm positioning sleeve is fastened to the set of opposing hook-and-loop material strips on the outer surface of the arm positioning sleeve to secure the arm positioning sleeve around the portion of the arm of the user. The arm positioning sleeve includes a body strap fastener. The body strap fastener includes a set of hook-and-loop fastener material strips on a portion of the outer surface of the arm positioning sleeve. The set of hook-and-loop fastener material strips are fastened to opposing hook-and-loop material on an inner surface of a set of body straps.

Still another illustrative embodiment provides a method for positioning a patient. An arm positioning sleeve is wrapped around a portion of an arm of a user. The arm positioning sleeve includes an outer surface and an inner surface. A set of arm sleeve fasteners is fastened to secure the arm positioning sleeve around the portion of the arm of the user. The arm of the user wrapped in the arm positioning sleeve is placed in a desired position. The outer surface of the arm positioning sleeve includes a set of hook-and-loop fastener material strips. A set of body straps is rotated over a torso of the user. Each body strap in the set of body straps comprises an outer surface and an inner surface. The inner surface of the each body strap in the set of body straps comprises a set of opposing hook-and-loop material strips. The set of hook and-loop fastener material strips on the outer surface of the arm positioning sleeve are fastened to the set of opposing hook-and-loop material strips on the inner surface of each body strap in the set of body straps to secure the arm of the user in the desired position.

BRIEF DESCRIPTION OF THE DRAWINGS

The novel features believed characteristic of the invention are set forth in the appended claims. The illustrative embodiments, as well as a preferred mode of use, further objectives and advantages thereof, will best be understood with reference to the following detailed description when read in conjunction with the accompanying drawings, wherein:

DETAILED DESCRIPTION

The different illustrative embodiments recognize and take into account a number of different considerations. For example, the different illustrative embodiments recognize and take into account that during medical procedures it is typically necessary to position and secure the arms of a patient to prevent pressure on the arms. The illustrative embodiments recognize that improperly positioned arms may cause pressure on motionless limbs and upper extremities. Arms containing intravenous lines can move, causing malfunction of the intravenous line and patient monitoring systems.

Current methods for positioning a patient's torso and arms frequently involve wrapping a sheet around an arm and tucking the sheet under the patient's body. However, the different illustrative embodiments recognize and take into account that the sheet tucked under the patient's torso frequently loosens and thereby may necessitate adjustment or re-positioning of the arm(s) and sheet(s) during the medical procedure.

Another current method involves positioning and securing a patient in a particular position using tape. The different illustrative embodiments recognize and take into account that tape may be time consuming to apply, time consuming to remove, and may frequently permit the patient's arms to move or slip out of the desired position.

Yet another current method for positioning the torso and limbs of a patient involves the use of sleds. A sled may be a metal or plastic device designed to immobilize the patient's arm. The different illustrative embodiments recognize and take into account that sleds may be cumbersome and obstruct medical personnel's access to the patient's body. The different illustrative embodiments also recognize and take into account that a sled may also slip out of the desired position and require adjustment and/or repositioning of the patient's arm during the medical procedure. The illustrative embodiments recognize these positioning systems are inflexible and preformed, losing the important advantage of adjustability.

In still another currently used method for positioning a patient, an assistant may hold the patient's arm in the desired position. However, this method may be time consuming, inefficient, and tiring for the assistant. The different illustrative embodiments recognize and take into account that the assistant may obstruct access to the patient by other medical personnel. In addition, the assistant may not be able to hold the patient's arm rigidly and precisely in the desired position.

The different illustrative embodiments also recognize that an increasing number of patients suffer from excessive weight. The embodiments recognize that, due to their size, these larger patients pose additional difficulties for positioning and securing the patient's arms. Attempts to position and immobilize the upper extremities in a large patient may be unsuccessful with sheets or sleds. The patient may overhang the surgical table, leaving no place for the arms. Moreover, the illustrative embodiments also recognize that sub-optimal positioning of the arms may cause pressure injury to the nerves and skin. Arms hanging outside or over the edge of the operating table can interfere with the surgeon's position and access to the patient.

Thus, the illustrative embodiments recognize that currently available methods for positioning and securing the arms of a patient frequently result in sub-optimal positioning and support of the patient's arms and shoulders. The embodiments recognize that currently available methods for positioning and securing the arms of a patient may require adjustment or re-positioning of the arms during a medical procedure due to slippage or loosening of the device used to position the arms. The different illustrative embodiments also recognize that currently available arm positioning techniques and devices are cumbersome and may interfere with the stance of a surgeon and other medical personnel in the operative field.

The different illustrative embodiments recognize that a need exists for a patient positioning system that allows rapid, secure and safe positioning of a patient's arms without interfering with access by medical personnel. Therefore, the illustrative embodiments provide a method, system, and apparatus for positioning a patient.

Figure 1:
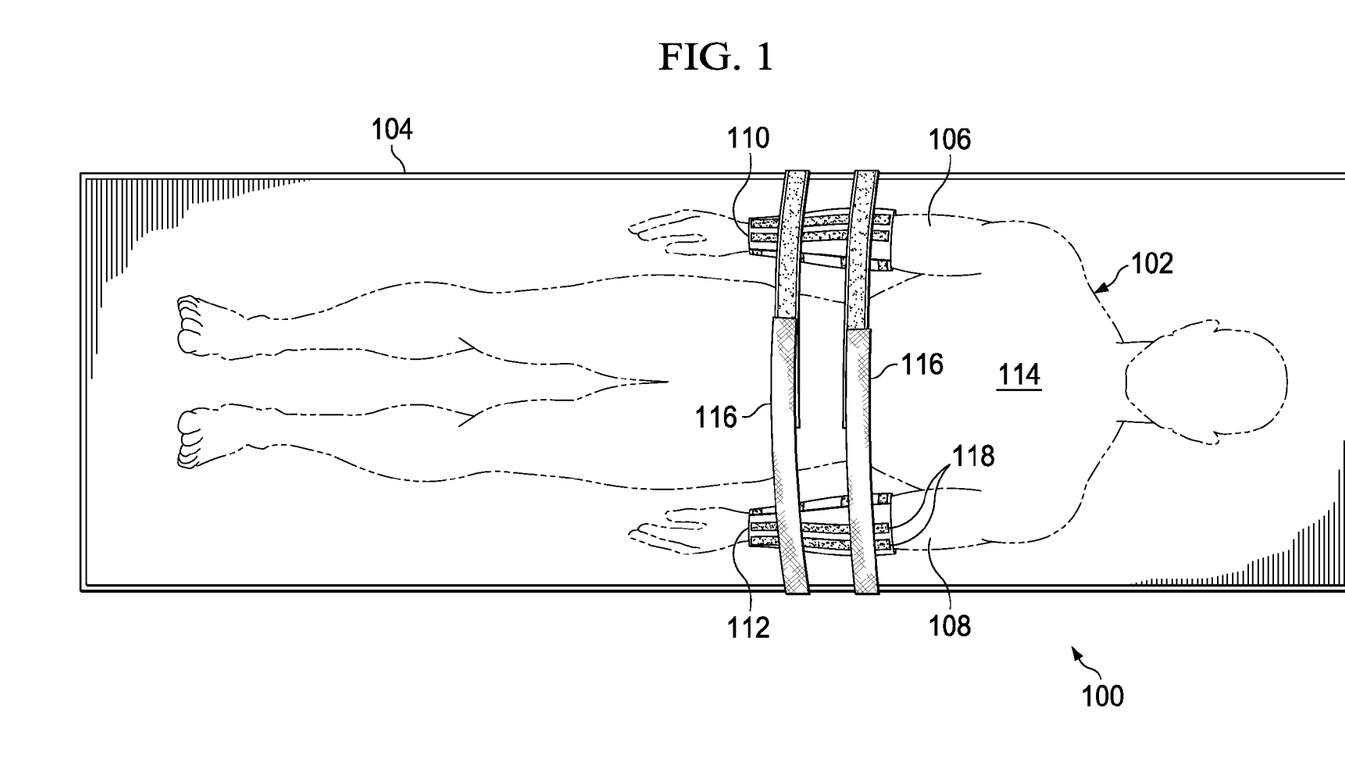
FIG. 1 is an illustration of a patient positioning system in accordance with an illustrative embodiment.

Referring now to the figures, FIG. 1 is an illustration of a patient positioning system in accordance with an illustrative embodiment. Arm positioning system 100 is a system for positioning and securing user 102 on operating table 104 for performance of a medical procedure.

User 102 is a patient undergoing a medical procedure or a patient that is being prepared to undergo a medical procedure. User 102 may be an adult, a child, an adolescent, a toddler, or an infant. In the example shown in FIG. 1, user 102 is lying on operating table 104 in a supine position. However, the illustrative embodiments may also be implemented with user 102 lying in a prone position.

Operating table 104 may be implemented as any type of operating table, operating bed, examination table, or any other surface upon which a medical procedure may be performed. A medical procedure may refer to an operation, surgery, an in-patient medical procedure, an out-patient medical procedure, or any medical service that may require positioning and securing of upper extremities of user 102.

When user 102 is placed on operating table 104, arm boards (not shown) may optionally be used to hold arms 106 and 108 in place during induction of anesthesia and other pre-surgical events. An arm positioning sleeve, such as arm positioning sleeve 110 or 112 is placed on an arm of user 102.

Figure 6:
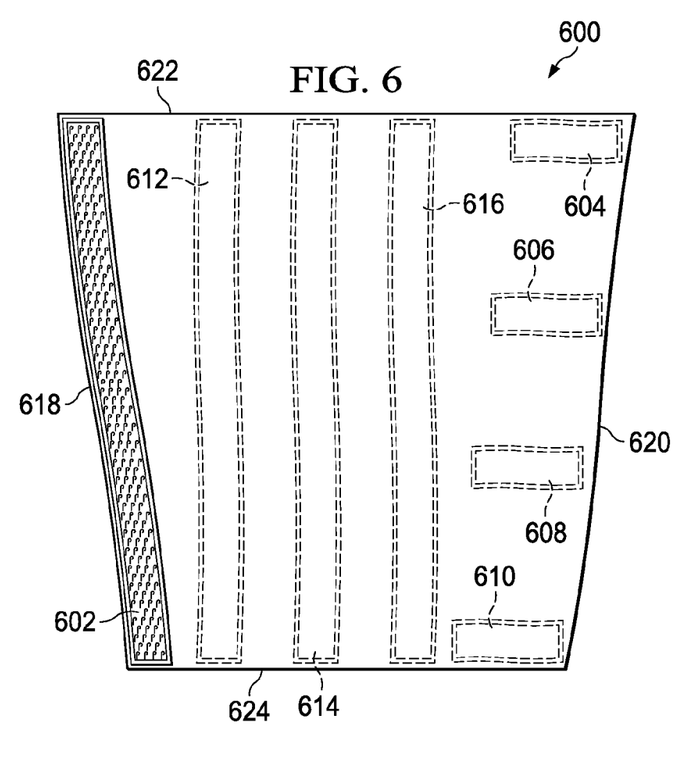
FIG. 6 is an illustration of an arm positioning sleeve in accordance with an illustrative embodiment.

In this example, arm positioning sleeve 110 is wrapped around arm 106. Arm positioning sleeve 110 is secured around arm 106 with an arm sleeve fastener on arm positioning sleeve 110. An example of an arm sleeve fastener is shown in FIG. 6 below.

In this non-limiting embodiment, the arm sleeve fastener is a hook-and-loop fastener. Hook-and-loop fasteners are fasteners that typically consist of two fabric hook-and-loop material strips attached to opposing surfaces that are to be fastened together. As used herein, the term "hook-and-loop fastener material" refers to material used in a hook-and-loop fastener system. Hook-and-loop fastener material may be implemented as hook material, loop material, or hooks-and-loops material. The term "opposing hook-and-loop material" also refers to material used in a hook-and-loop fastener system. Opposing hook-and-loop material may be implemented as hook material, loop material, or hooks-and-loops material that is capable of fastening to an associated hook-and-loop fastener material.

Hook material is material having a plurality of tiny hooks capable of fastening to loops on opposing hook-and-loop material. Loop material is material having a plurality of tiny loops capable of fastening to hooks on opposing hook-and-loop material. When hook material is brought into contact with loop material, the tiny hooks on the hook material binds to the tiny loops on the loop material to form a bond or fastener. Hooks-and-loops material is material having both a plurality of tiny hooks and a plurality of tiny loops together on the same surface of the material. In other words, hooks-and-loops material has both hooks and loops together on one or more faces of the material.

When hook-and-loop fastener material is joined to the opposing hook-and-loop material, the portion of the hook-and-loop fastener material in contact with a portion of the opposing hook-and-loop material binds together creating a hook-and-loop fastener. The opposing hook-and-loop material is a material that is capable of fastening to the hook-andloop fastener material. If the hook-and-loop fastener material has only hooks on the surface of the material to be joined to the opposing hook-and-loop material, then the opposing hook-and-loop material includes loops on the surface of the opposing hook-and-loop material that is capable of being joined or fastened to the hooks on the hook-and-loop fastener material.

In other words, if the hook-and-loop fastener material is hook material, then the opposing hook-and-loop material may only be loop material or hooks-and-loops material which can fasten to the hooks in the hook material. In this example, the opposing hook-and-loop material may not also be hook material, as hook material is not capable of fastening to another piece of hook material.

Likewise, if the hook-and-loop fastener material is loop material having only loops on the surface to be joined to the opposing hook-and-loop material, then the opposing hook-and-loop material may be hook material or hooks-and-loops material having hooks on its surface that are capable of fastening to the loops in the hook-and-loop fastener material.

In yet another example, if the hook-and-loop fastener material is a hooks-and-loops material, the hooks-and-loops material may be brought into contact with opposing hook-and-loop material that may be hook material, loop material, or another piece of hooks-and-loops material to create a bond between the hook-and-loop fastener material and the opposing hook-and-loop material.

Hook-and-loop fasteners may be glued on to a surface, taped onto a surface, sewn on to a fabric surface, or otherwise attached to a surface with adhesive. Hook-and-loop fastener systems may also be referred to as hook-and-eye fasteners, hook and receiver, hook tape and loop tape, and other variations. An example of a hook-and-loop fastener system is, without limitation, the Velcro® brand hook-and-loop fasteners.

In this example, arm positioning sleeve 110 covers a portion of the arm of user 102 from the wrist to a point above the elbow of the user. In another embodiment, arm positioning sleeve 110 may cover arm 106 from the wrist to a point on the upper arm in proximity to the under-arm area. In still another non-limiting embodiment, arm positioning sleeve 110 covers the entire arm 106 from the wrist to a point near the shoulder. In yet another different embodiment, arm positioning sleeve 110 covers a portion of arm 106 from the wrist to the elbow.

Once arms 106 and 108 are wrapped in a fastened arm positioning sleeve, medical personnel place arms 106 and 108 in a desired position relative to torso 114. The desired position is a position that is desired, recommended, or preferred for a particular medical procedure. The desired position may involve positioning arms 106 and/or 108 at the user's sides as shown in FIG. 1. However, in another non-limiting illustrative embodiment, the desired position may involve positioning one or both of arms 106 and/or 108 across torso 114, folded over the chest of user 102, or placed over the body of user 102 rather than placed at one or more sides of user 102.

Set of body straps 116 is a set of one or more straps. As used herein, the term "set" refers to one or more items. In this embodiment, set of body straps 116 may include a single body strap, as well as two or more body straps.

Each body strap in set of body straps 116 is affixed at one end to operating table 104. A body strap is affixed to operating table 104 by connecting or attaching one end of the body strap to a part of operating table 104. For example, but without limitation, a body strap may be connected at one end to a bed rail (not shown) of operating table 104. The body strap may also be connected to an anchor on operating table 104 or any other part of operating table 104.

In this non-limiting embodiment, each body strap in set of body straps 116 is slidably affixed at one end to operating table 104. The term slidably affixed refers to the ability to adjust the location on operating table 104 at which one end of a body strap is attached. In other words, the end of a body strap attached to operating table 104 may be moved up and down the sides of operating table 104 to adjust the placement of the body strap. This adjustability of the location at which a body strap is affixed to operating table 104 permits set of body straps 116 to be adjusted to accommodate very large, adult patients, as well as smaller patients, such as petite adults, teenagers, infants, toddlers, and children. Set of body straps 116 may also be slidably adjusted to accommodate certain configurations of arms 106 and/or 108 that may require one or more body straps be adjusted up or down the length of operating table 104. At least one surface of each strap in set of body straps 116 includes hook-and-loop fastener material. The hook-and-loop fastener material may be hook material having only hooks, loop material having only loops, or hooks-and-loops material having both hooks and loops together on the same surface of the material.

Each arm positioning sleeve 110 and 112 includes a set of opposing hook-and-loop material strips 118 on the outer surface of the arm positioning sleeve. Set of opposing hook-and-loop material strips 118 in this example includes two strips of opposing hook-and-loop material capable of fastening to the hook-and-loop fastener material on set of body straps 116. However, in another illustrative embodiment, set of opposing hook-and-loop material strips on the outer surface of arm positioning sleeve 110 and/or 112 may include a single opposing hook-and-loop material strip. In yet another illustrative embodiment, arm positioning sleeve 110 and/or 112 may include three or more strips of opposing hook-and-loop material on the outer surface of the arm positioning sleeve.

Each body strap in set of body straps 116 includes at least one strip of hook-and-loop fastener material on at least one surface of the body strap. A body strap has two surfaces, an inner surface and an outer surface. An inner surface is a surface that may be in partial contact with user 102 and/or one or more arm sleeves when the body strap is wrapped around user 102. An outer surface is a surface that is not in contact with user 102 when the body strap is wrapped around user 102. In other words, an outer surface is visible or displayed outward when the body strap is wrapped around user 102. The hook-and-loop fastener material may be located on the inner surface of the body strap and/or on the outer surface of the body strap.

Arm positioning sleeve 110 and 112 include set of opposing hook-and-loop material strips. Each body strap in set of body straps 116 is draped over and across torso 114 of user 102. The hook-and-loop fastener material on an inner surface of one or more body straps is secured to opposing hook-and-loop material in set of opposing hook-and-loop material strips 118 on each of arm positioning sleeves 110 and 112. The hook-and-loop fastener material on set of body straps 116 is fastened to opposing hook-and-loop material on arm positioning sleeves 110 and 112 to form a hook-and-loop fastener fastening the arm positioning sleeves to at least one body strap.

Set of body straps 116 is fastened to both arm positioning sleeves 110 and connected to operating table 104, user's arms and torso 114 are held safely and securely in position. In this manner, arms 106 and 108 are immobilized in the desired position for the remainder of the medical procedure. The positioning and stability of the arms relative to the patient's torso also improves reliability of intravenous catheters Moreover, the position of arms 106 and 108 relative to torso 114 and operating table 104 is rendered completely adjustable. After application of the arm positioning sleeves 110 and 112 and set of body straps 116, further prepping and draping of user 102 and operative site may proceed as usual.

In one non-limiting embodiment, arm positioning sleeves 110 and 112 are disposable. The disposable arm positioning sleeves may be single use sleeves. After the medical procedure is complete, arm positioning sleeves 110 and 112 and set of body straps 116 may be removed quickly and disposed of safely. This disposability permits rapid removal and also decreases or eliminates cross-contamination in successive surgeries.

Thus, arm positioning sleeves 110 and 112 and set of body straps 116 in this non-limiting embodiment assembly together around user 102 such that the upper extremities of user 102 are held securely, conveniently, accurately, and safely on operating table 104.

In the embodiment shown in FIG. 1, a positioning arm sleeve is placed on both arms 106 and 108 of user 102. However, in another embodiment, only a single arm positioning sleeve may be used to position only one arm of user 102. In other words, in a different illustrative embodiment, a single arm positioning sleeve may be used on only one arm rather utilizing two arm positioning sleeves.

Figure 2:
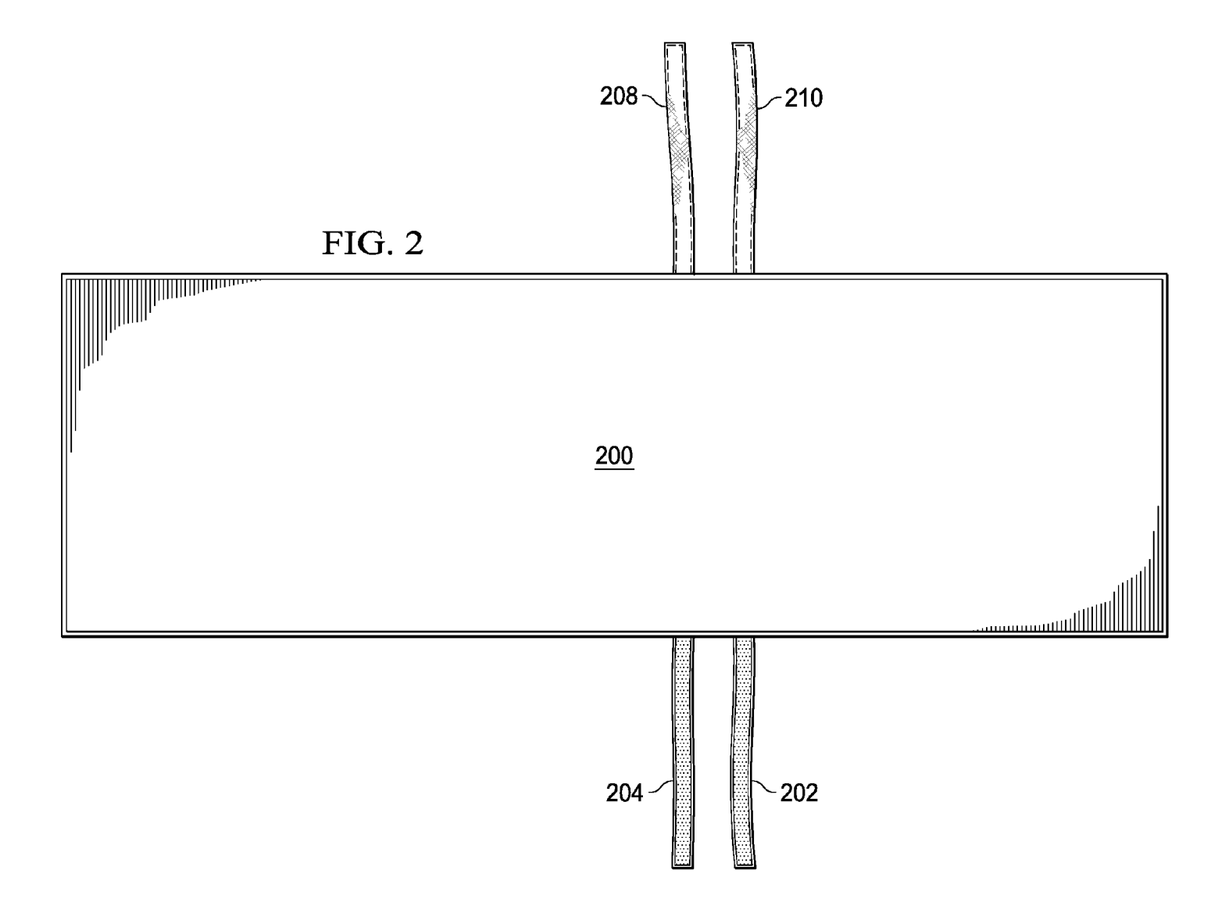
FIG. 2 is an illustration of a set of body straps in accordance with an illustrative embodiment.

FIG. 2 is an illustration of a set of body straps in accordance with an illustrative embodiment. FIG. 2 shows a view of operating table 200 from above. An inner surface of body straps 202, 204, 208, and 210 is shown here in FIG. 2.

Operating table 200 is a table for performing a medical procedure, such as, but without limitation, operating table 104 in FIG. 1. Operating table 200 may be implemented as any type of operating table, operating bed, examination table, or any other surface upon which a medical procedure may be performed.

In this embodiment, a set of body straps is connected to both sides of operating table 200. In one non-limiting embodiment, the set of body straps includes body straps 202, 204, 208, and 210. Each body strap includes one side of the body strap covered in hook-and-loop fastener material and a second side of the body strap covered in opposing hook-and-loop material to form a body strap fastener.

In this non-limiting example, when a user is lying on operating table 200 and wearing a set of arm positioning sleeves, each body strap is rotated over the user's torso. A portion of the hook-and-loop fastener material on one side of one body strap is attached to a portion of the opposing hook-and-loop material on an outer surface of each arm positioning sleeves, as shown in FIG. 1. Each body strap is also fastened to another body strap connected to an opposite side of operating table 200 using the body strap fasteners.

In the non-limiting illustrative embodiment shown here in FIG. 2, a body strap attached to one side of operating table 200 includes hook-and-loop fastener material and a body strap attached to the opposite side of operating table 200 has opposing hook-and-loop material. For example, but without limitation, body straps 202 and 204 on one side of operating table 200 may have hook material on an inner surface while body straps 208 and 210 on the opposite side of operating table 200 have loop material on both the inner surface and the outer surface. A portion of the hook material on the inner surface of body strap 210 is attached to a portion of the loop material on the outer surface of body strap 202 to fasten body straps 202 and 210 together. Connecting a portion of the loop material on body strap 210 to a portion of the hook material on body strap 202 fastens body strap 202 to body strap 210. As used herein, the term portion may refer to only a part of the hook-and-loop fastener material. The term portion may also refer to all of a strip of hook-and-loop fastener material.

In this non-limiting embodiment, body strap 204 is rotated over a user lying on operating table 200 and fastened to body strap 208 by the body strap hook-and-loop fastener. Body strap 204 is fastened to body strap 208 by fastening opposing hook-and-loop material on body strap 208 to the hook-and-loop fastener material on body strap 204. Likewise, body strap 202 may be rotated over the user and fastened to body strap 210 by fastening the hook-and-loop fastener material on body strap 202 to the opposing hook-and-loop material on body strap 210.

In this embodiment, the width of each body strap is about three inches wide. However, in a different embodiment, each body strap may be a width within a range of one to six inches. The width of the body straps may be determined based upon a weight or mass of the patient and/or the weight or mass of the patient's arms. For example, smaller patients, such as children or slender adults, may only require one inch thick body straps, whereas larger and heavier patients may require the use of body straps that are closer to six inches in width.

In another exemplary embodiment, operating table 200 includes at least two disposable and adjustable body straps that attach to the arm rails on operating table 200. Each body strap is adjustably fastened to another body strap on the opposite side of operating table 200 to adjust the length of the body straps wrapped over the user's torso and arms.

Figure 3:
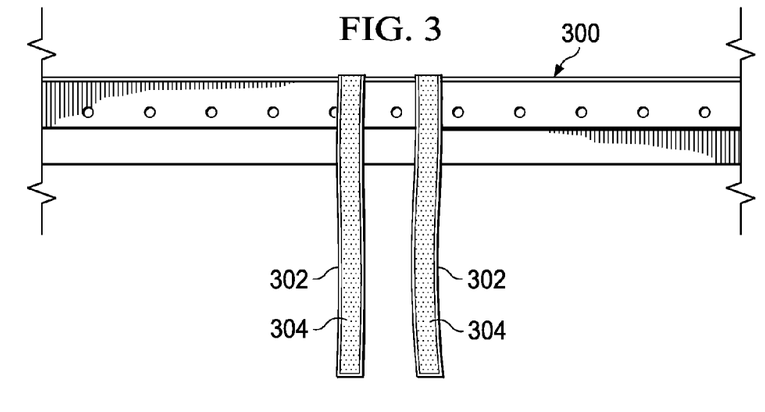
FIG. 3 is an illustration of a set of body straps slidably affixed to an operating table in accordance with an illustrative embodiment.

Turning now to FIG. 3, an illustration of a set of body straps slidably affixed to an operating table is shown in accordance with an illustrative embodiment. FIG. 3 shows a side view of operating table 300.

Operating table 300 is a table for performing a medical procedure, such as, but without limitation, operating table 104 in FIG. 1 and operating table 200 in FIG. 2. Operating table 300 may be implemented as any type of operating table, operating bed, examination table, or any other surface upon which a medical procedure may be performed.

Operating table 300 has set of body straps 302. Set of body straps 302 in this non-limiting example, includes two body straps on one side of operating table 300. However, in another embodiment, operating table 300 may have only a single body strap on one side of operating table 300. In yet another embodiment set of body straps 302 may include three or more body straps connected to each side of operating table 300.

In this non-limiting embodiment, each body strap in set of body straps 302 is slidably affixed at one end to operating table 300. Each body strap may be slidably adjusted at the point of attachment to operating table 300. In other words, each body strap may be moved to the left or right along a side of operating table by the end affixed to operating table 300. For example, a given body strap may be attached to operating table 300 at a point about midway between each end of operating table 300, as shown here in FIG. 3. The given body strap may be adjusted to the left or right along the side of operating table 300 to affix the given body strap at a point closer to one end of operating table 300 or along any other position along the side of operating table 300.

However, in another non-limiting embodiment, one or more body straps in set of body straps 116 may be fixedly attached at one end to operating table 300. A body strap that is fixedly attached is fixed at one point or location on operating table 300 and may not be adjusted.

Prior to use, each body strap in set of body straps 302 hangs down on either side of operating table 300. In one non-limiting embodiment, the length of body strap is long enough to wrap completely around the user lying on operating table 300 without touching the floor when the body strap is hanging loosely off the side of the operating table 300. In another non-limiting embodiment, the length of a first body strap attached by one end of the first body strap to the right side of operating table 300 is long enough to attach to an opposing second body strap attached by one end of the second body strap to the left side of operating table 300.

In this non-limiting illustrative embodiment, the length of each body strap is about thirty inches long. In a different non-limiting embodiment, each body strap in set of body straps 302 may be a length within a range of twelve inches to forty-eight inches. In still another embodiment, each body strap in set of body straps 302 may be a different length.

Each body strap in set of body straps 302 includes at least one strip of hook-and-loop fastener material 304 on at least one surface. Hook-and-loop fastener material 304 may be implemented as hook material having only hooks, loop material having only loops, or hooks-and-loops material having both hooks and loops together.

In this non-limiting embodiment, hook-and-loop fastener material 304 is shown on an inner surface of each body strap in set of body straps 302. In a different embodiment, each body strap in set of body straps 302 may include hook-and-loop fastener material on one side and opposing hook-and-loop material on the opposite side of each body strap.

Figure 4:
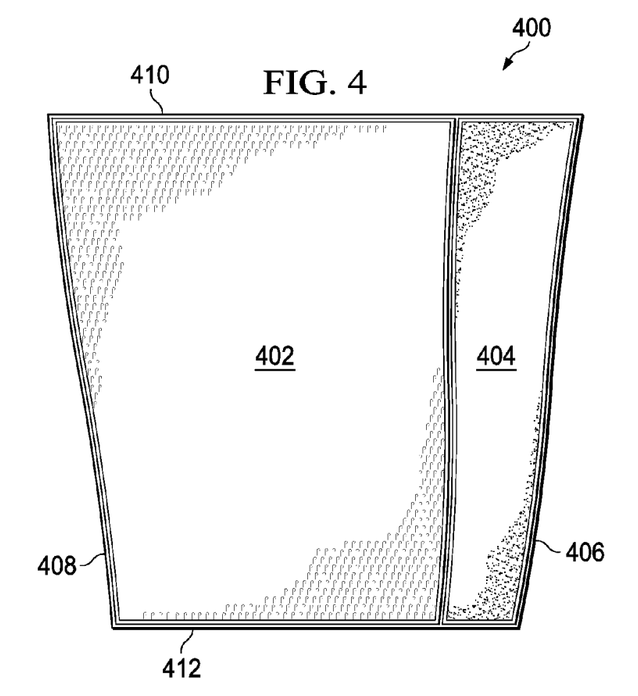
FIG. 4 is an illustration of an outer surface of an arm positioning sleeve in accordance with an illustrative embodiment.

Referring now to FIG. 4, an illustration of an outer surface of an arm positioning sleeve in accordance with an illustrative embodiment. FIG. 4 is a view of an outer surface of arm positioning sleeve 400 rolled out before arm positioning sleeve 400 is wrapped around a user's arm. The outer surface is the surface facing away from the user's arm when the arm positioning sleeve is wrapped around the user's arm while in use. Arm positioning sleeve 400 is an arm positioning sleeve, such as arm positioning sleeve 110 and 112 in FIG. 1.

The outer surface of arm positioning sleeve 400 includes at least one hook-and-loop fastener material strip 402 of a body sleeve fastener. The hook-and-loop fastener material strip 402 may be implemented as a hook material strip, a loop material strip, or a hooks-and-loops material strip. In this non-limiting embodiment, the at least one hook-and-loop fastener material strip 402 on the outer surface of arm positioning sleeve 400 is implemented as a hook material strip 402 including a plurality of hooks for binding to at least one opposing hook-and-loop material on the inner surface of a body strap, such as body straps 202, 204, 208, and 210 in FIG. 2. The opposing hook-and-loop material on at least one body strap (not shown) is fastened to hook-and-loop fastener material strip 402 to secure an arm sleeve in a desired position. An opposing hook-and-loop material on a body strap is shown in FIG. 2 and FIG. 3 above.

Figure 5:
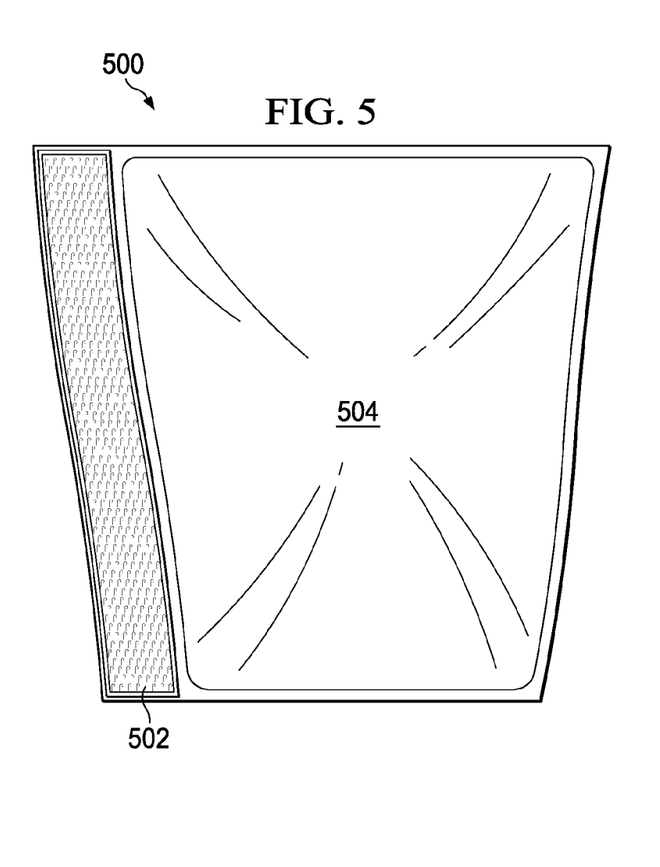
FIG. 5 is an illustration of an inner surface of an arm positioning sleeve in accordance with an illustrative embodiment.

The outer surface of arm positioning sleeve 400 includes at least one hook-and-loop fastener material strip 404 of an arm sleeve fastener. Hook-and-loop fastener material strip 404 may be fastened to a set of opposing hook-and-loop material strips located on the inner surface (not shown) of arm positioning sleeve 400 to fasten arm positioning sleeve 400 around the user's arm. An inner surface of arm positioning sleeve 400 is shown in FIG. 5 below.

In this non-limiting embodiment, hook-and-loop fastener material strip 404 includes at least one loop material strip. In this example, the loop material strip fastens to opposing hook material located on the inner surface of arm positioning sleeve 400. However, in another embodiment, hook-and-loop fastener material strip 404 may be at least one hook material strip that fastens to opposing loop material on the inner surface of arm positioning sleeve 400. In still another non-limiting embodiment, hook-and-loop fastener material strip 404 may be implemented as hooks-and-loops material that fastens to opposing hook-and-loop material on the inner surface of arm positioning sleeve 400

Arm positioning sleeve 400 in this embodiment is four sided and tapered to conform to human anatomy. First longitudinal side 406 is opposite to second longitudinal side 408. First end 410 is opposite to second end 412. In this non-limiting embodiment, first end 410 has a greater length than second end 412. In this non-limiting example, first longitudinal side 406 and second longitudinal side 408 are tapering from first end 410 to second end 412.

Furthermore, second end 412 is positioned around the portion of the arm closer to the wrist when in use, whereas second end 410 is positioned around the portion of the arm away from the wrist, such as the forearm, elbow, or bicep, depending upon the particular configuration of arm positioning sleeve 400.

In this non-limiting embodiment, hook-and-loop material strip 402 and 404 on the outer surface of arm positioning sleeve 400 is implemented as hook-and-loop fastener material covering substantially the entire outer surface of arm positioning sleeve. In yet another embodiment, hook-and-loop fastener material strip 402 and 404 on the outer surface of arm positioning sleeve 400 is implemented as hooks-and-loops fastener material covering a portion of the outer surface of arm positioning sleeve 400. In other words, hook-and-loop material strip 402 and 404 may not cover substantially the entire outer surface of arm positioning sleeve 300.

FIG. 5 is an illustration of an inner surface of an arm positioning sleeve in accordance with an illustrative embodiment. FIG. 5 is a view of an inner surface of an arm positioning sleeve before the arm positioning sleeve is wrapped around a user's arm. The inner surface is the surface facing the user's arm when the arm positioning sleeve is wrapped around the user's arm. A portion of the inner surface may be in contact with the user's arm while the arm positioning sleeve is wrapped around the user's arm. Arm positioning sleeve 500 is an arm positioning sleeve, such as arm positioning sleeve 110 and 112 in FIG. 1, and arm positioning sleeve 400 in FIG. 4.

The inner surface of arm positioning sleeve 500 includes at least one opposing hook-and-loop material strip 502. When arm positioning sleeve 500 is wrapped around a user's arm, opposing hook-and-loop material strip 502 is fastened to one or more hook-and-loop fastener material strips on the outer surface of arm positioning sleeve 500, such as the at least one hook-and-loop fastener material strip 404 in FIG. 4.

In this non-limiting embodiment, the inner surface of arm positioning sleeve 400 also includes padding 504. Padding 504 is located on the inner surface where the inner surface contacts the arm of the user when arm positioning sleeve 500 is wrapped around the user's arm. Padding 504 may be made of any type of soft, disposable, padding material, such as, for example and without limitation, padding foam and cotton. The padded arm positioning sleeve 500 holds the arm securely and also fastens to the body straps securely with the hook-and-loop body strap fasteners.

Padding 504 provides improved patient comfort and safety. The soft, padded inner lining provided by padding 504 cushions the user's arm and decreases pressure points on the arms. Padding 504 minimizes skin shear and potential injuries of nerves and skin that may occur while the user is anesthetized and motionless.

Turning now to FIG. 6, an illustration of an arm positioning sleeve is shown in accordance with an illustrative embodiment. FIG. 6 is a view of arm positioning sleeve 600 showing both an inner surface and a superimposed partial outer surface of arm positioning sleeve 600. Arm positioning sleeve 600 is an arm positioning sleeve, such as arm positioning sleeve 110 and 112 in FIG. 1.

Hook-and-loop fastener material strip 602 is a strip of hook-and-loop material located on an inner surface of arm positioning sleeve 600. In this non-limiting embodiment, hook-and-loop fastener material strip 602 is implemented as hook material. However, in another embodiment, hook -and-loop fastener material strip 602 may be implemented as loop material or hooks-and-loops material.

Hook-and-loop fastener material strip 602 is part of an arm sleeve fastener. Hook and loop fastener material strip 602 binds to one or more opposing hook-and-loop material strips, such as, but without limitation, opposing hook-and-loop material strips 604, 606, 608, and 610. Hook-and-loop fastener strip 602 is fastened to one or more of opposing hook-and-loop material strips 604, 606, 608, and 610 to fasten arm positioning sleeve 600 around an arm of a user. When arm positioning sleeve 600 is wrapped around a portion of a user's arm, hook-and-loop fastener material strip 602 on the inner surface is fastened to at least one of opposing hook-and-loop material strips 604, 606, 608, and 610 on the outer surface of arm positioning sleeve 600 to secure the arm positioning sleeve around the arm of the user.

In this non-limiting embodiment, hook-and-loop fastener material strip 602 is seventeen inches long and two inches wide. However, in another illustrative embodiment, hook-and-loop fastener material strip 602 may have a length in a range of six to twenty-four inches and a width in a range of one to six inches.

Arm positioning sleeve 600 includes a set of hook-and-loop fastener material strips on an outer surface of arm positioning sleeve 600 and located on the outer surface of arm positioning sleeve 600, along the longitudinal side opposite hook-and-loop fastener material strip 602. The set of hook-and-loop fastener material strips may include a single strip of hook-and-loop fastener material, as well as two or more strips of hook-and-loop fastener material. In this non-limiting embodiment, the set of hook-and-loop fastener material strips includes four hook-and-loop fastener material strips 604, 606, 608, and 610.

In this example, opposing hook-and-loop material strips 604, 606, 608, and 610 are about two inches long and six inches wide. However, in another embodiment, opposing hook-and-loop material strips 604, 606, 608, and 610 may have a length in a range of six to twenty-four inches and a width in a range of one to six inches.

Arm positioning sleeve 600 includes a set of hook-and-loop fastener material strips on a portion of the outer surface of arm positioning sleeve 600. The set of hook-and-loop fastener material strips are part of a body strap fastener used to fasten a set of body straps to arm positioning sleeve 600. Hook-and-loop fastener material strips 612, 614, and 616 are fastened to opposing hook-and-loop material on a set of body straps, such as, but without limitation, set of body straps 116 in FIG. 1, body straps 202-210 in FIG. 2, or set of body straps 302 in FIG. 2.

Hook-and-loop fastener material strips 612, 614, and 616 in this embodiment are implemented as hook material strips. However, in a different embodiment, hook-and-loop material strips 612, 614, and 616 may be implemented using loop material strips or hooks-and-loops material strips.

In this non-limiting example, each hook-and-loop fastener material strip 612, 614, and 616 is about seventeen inches long and two inches wide. However, in another embodiment, hook-and-loop fastener material strips have a length in a range of six to twenty-four inches and a width in a range of one to six inches.

In this non-limiting illustrative embodiment, arm positioning sleeve 600 is about seventeen inches long on the longitudinal sides 618 and 620. Arm positioning sleeve 600 is about twenty-four inches wide at first end 622 and about eighteen inches wide at second end 624. However, in another illustrative embodiment, longitudinal sides 618 and 620 may have a length in a range of six inches to thirty inches. In yet another embodiment, end 622 and 624 may have a width in a range from six inches to thirty inches.

In the non-limiting embodiment shown in FIG. 6, arm positioning sleeve 600 includes a single hook-and-loop fastener material strip for the arm sleeve fastener. However, in another embodiment, the arm sleeve fastener for arm positioning sleeve 600 may include two or more hook-and-loop fastener material strips.

In this non-limiting example, arm positioning sleeve 600 is shown with four opposing hook-and-loop material strips 604, 606, 608, and 610 for the arm sleeve fastener. However, in a different embodiment, the arm sleeve fastener for arm positioning sleeve 600 may include one or more opposing hook-and-loop material strips for the arm sleeve fastener.

In this illustrative example in FIG. 6, arm positioning sleeve 600 includes three hook-and-loop fastener material strips for the body sleeve fastener. However, the illustrative embodiments are not limited to having three hook-and-loop fastener material strips for the body sleeve fastener. The arm positioning sleeve 600 may be implemented having only a single hook-and-loop fastener material strip for the body sleeve fastener, as well as two or more hook-and-loop fastener material strips for the body sleeve fastener.

Figure 7A:
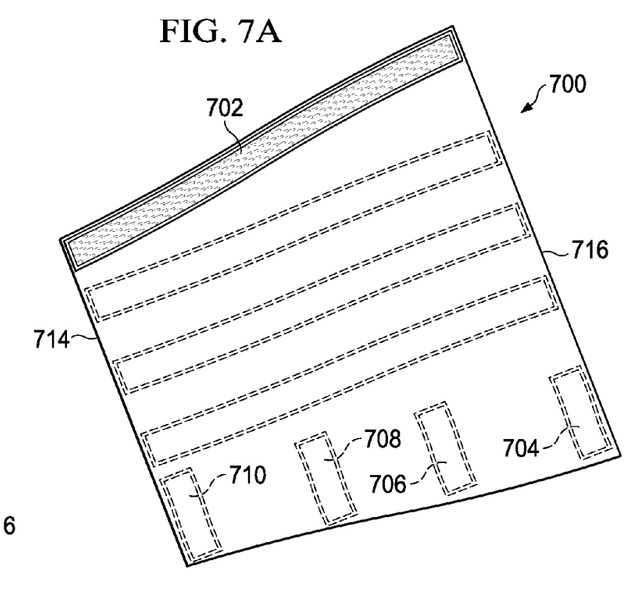
FIG. 7A is an illustration of a set of arm sleeve fasteners of an arm positioning sleeve in accordance with an illustrative embodiment.

FIG. 7A is an illustration of a set of arm sleeve fasteners of an arm positioning sleeve in accordance with an illustrative embodiment. Arm positioning sleeve 700 is a sleeve for positioning and securing an arm of a user, such as arm positioning sleeve 110 and 112 in FIG. 1 and arm positioning sleeve 600 in FIG. 6.

A user fastens hook-and-loop fastener material strip 702 on the inner surface of arm positioning sleeve 700 to one or more opposing hook-and-loop material strips 704, 706, 708, and 710 on the outer surface of arm positioning sleeve 700 to fasten arm positioning sleeve 700 around a user's arm.

Hook-and-loop fastener material strip 702 may be implemented as hook material, loop material, or hooks-and-loops material. In this non-limiting example, hook-and-loop fastener material strip 702 implemented as a strip of hook material.

Opposing hook-and-loop material strips material strips 704, 706, 708, and 710 on the outer surface of arm positioning sleeve 700 fasten to hook-and-loop fastener material strip 702 on the inner surface of arm positioning sleeve 700. Opposing hook-and-loop material strips material strips 704, 706, 708, and 710 may also be implemented as hook material strip(s), loop material strip(s), or hooks-and-loops material strip(s) that is capable of fastening or binding to hook-and-loop fastener material strip 702. In this non-limiting example, hook-and-loop fastener material strips 704, 706, 708, and 710 are shown implemented as loop material strips complementary to the hook material of hook-and-loop fastener material strip 702.

Figure 7B:
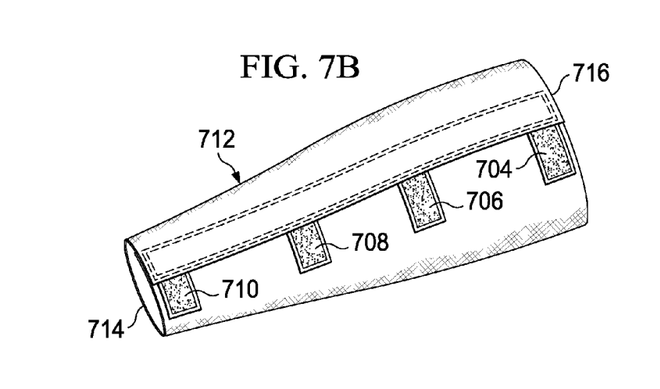
FIG. 7B is an illustration of the set of arm sleeve fasteners of the arm positioning sleeve fastened in accordance with an illustrative embodiment.

FIG. 7B is an illustration of the set of arm sleeve fasteners of the arm positioning sleeve fastened in accordance with an illustrative embodiment. Arm positioning sleeve 712 shows the arm positioning sleeve as it may appear when fastened around a user's arm. First end 714 of arm positioning sleeve has a greater circumference or width than second end 716. First end 714 corresponds with the region distal to the wrist, such as the forearm or the bicep. Second end 716 has a smaller circumference or width than first end 714. Second end 716 corresponds to the wrist region of the arm. When arm sleeve fastener is fastened, arm positioning sleeve 712 forms a tapering, cylindrical shape to conform to the shape of the human arm.

Figure 8:
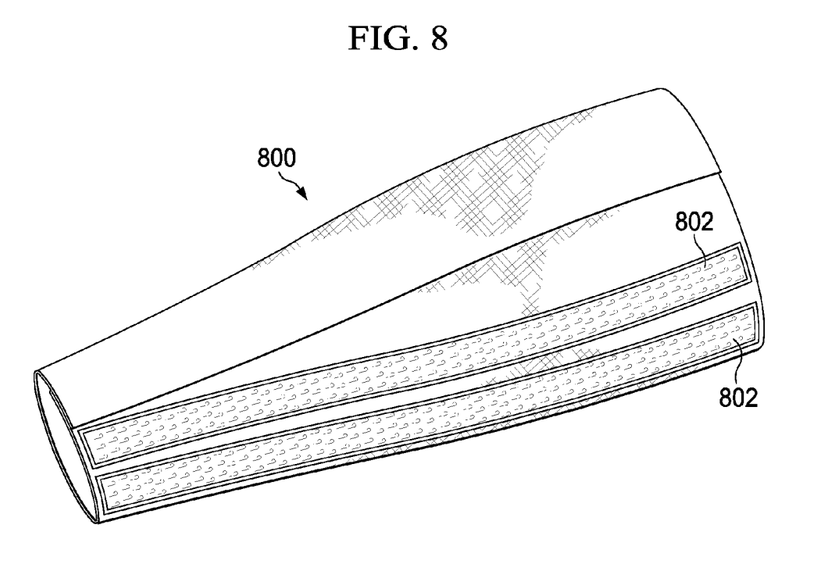
FIG. 8 is an illustration of a set of hook-and-loop fastener material strips on an arm positioning sleeve in accordance with an illustrative embodiment.

Turning now to FIG. 8, an illustration of a set of hook-and-loop fastener material strips on an arm positioning sleeve is shown in accordance with an illustrative embodiment. Arm positioning sleeve 800 is a sleeve for positioning and securing an arm of a user during a medical procedure, such as arm positioning sleeve 110 and 112 in FIG. 1, arm positioning sleeve 400 in FIG. 4, arm positioning sleeve 500 in FIG. 5, arm positioning sleeve 600 in FIG. 6, and arm positioning sleeve 700 in FIG. 7.

FIG. 8 shows a front side of arm positioning sleeve 800 in a wrapped, cylindrical form with the arm sleeve fasteners fastened. The front side is the outer surface of arm positioning sleeve that is exposed and visible when arm positioning sleeve 800 is wrapped around a user's arm. The back side of the outer portion of arm positioning sleeve 800 is underneath the user's arm and inaccessible when arm positioning sleeve is being worn by the user. In other words, the back side is the outer surface of arm positioning sleeve 800 that is beneath the user's arm and in contact with the operating table.

Opposing hook-and-loop material strips 802 are a set of one or more strips of hook-and-loop material capable of binding or fastening to hook-and-loop fastener material on one or more body straps. Opposing hook-and-loop material strips 802 fasten to hook-and-loop fastener material strips on one or more body straps, such as set of body straps 116 in FIG. 1, body straps 202-210 in FIG. 2, and set of body straps 302 in FIG. 3.

In this embodiment, opposing hook-and-loop material strips 802 includes two strips of hook-and-loop fastener material. In another illustrative embodiment, arm positioning sleeve may include one or more opposing hook-and-loop material strips. In this example, opposing hook-and-loop material strips 802 only cover a portion of the outer surface of arm positioning sleeve 800. In another non-limiting embodiment, opposing hook-and-loop material strips 802 may be implemented as a single hook-and-loop fastener material strip that covers substantially all of the front side of arm positioning sleeve 800.

Figure 9:
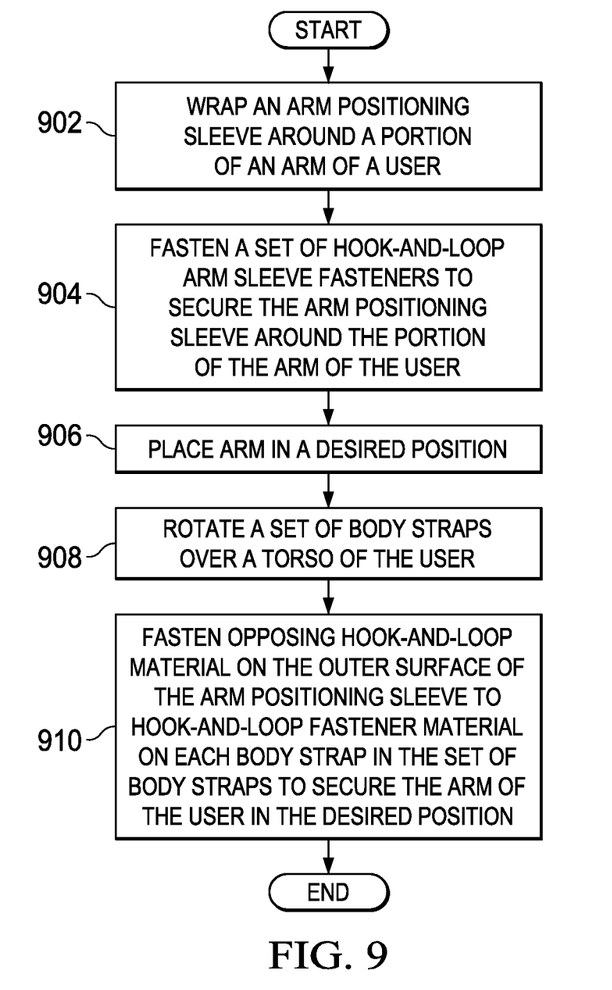
FIG. 9 is a flowchart illustrating a process for positioning a patient in accordance with an illustrative embodiment.

FIG. 9 is a flowchart illustrating a process for positioning a patient in accordance with an illustrative embodiment. The process in FIG. 9 may be implemented using an arm positioning system, such as arm positioning system 100 in FIG. 1.

The process begins by wrapping an arm positioning sleeve around a portion of an arm of a user (step 902). A set of hook-and-loop arm sleeve fasteners is fastened to secure the arm positioning sleeve around the portion of the arm of the user (step 904). The arm of the user is placed in a desired position (step 906). A set of body straps is rotated over a torso of the user (step 908). Opposing hook-and-loop material on the outer surface of the arm positioning sleeve are fastened to hook-and-loop fastener material on each body strap in the set of body straps to secure the arm of the user in the desired position (step 910) with the process terminating thereafter.

In this non-limiting embodiment in FIG. 9, the opposing hook-and-loop material on the outer surface of the arm positioning sleeve are implemented as hook fasteners on hook material and the hook-and-loop fastener material may be implemented as loop material capable of binding to the hooks on the opposing hook-and-loop material. In a different embodiment, the process in FIG. 9 may be implemented using loop material for the opposing hook-and-loop material on the arm positioning sleeve and hook material for the hook-and-loop fastener material on the set of body straps. In still another embodiment, the process in FIG. 9 may be implemented using hooks-and-loops material as the opposing hook-and-loop material on the outer surface of the arm positioning sleeve and the hook-and-loop fastener material on the set of body straps.

This method for positioning and securing the arms and torso of a patient allows for speed of application. This method is straightforward to implement. The method may also be implemented quickly, such as, for example, in about one minute or possibly less. This is a significant time savings when a patient is under general anesthesia.

One illustrative embodiment provides a system for patient positioning is provided. A set of arm positioning sleeves is provided. Each arm positioning sleeve in the set of arm positioning sleeves is wrapped around a portion of an arm of a user lying on an operating table. The term "wrapped" refers to the ability or capability of being wrapped or rolled up into a cylindrical form around a user's arm.

One end of each body strap in a set of body straps may be slidably connected to a set of rails of the operating table. A set of body strap fasteners is provided that includes a set of hook-and-loop fastener material strips attached to an inner surface of each body strap. A set of opposing hook-and-loop material strips is attached to a portion of an outer surface of each arm positioning sleeve. The set of opposing hook-and-loop material strips on the set of arm positioning sleeves fastens to the set of hook-and-loop fastener material strips on the set of body straps to secure each arm of the user lying on the operating table in a desired position.

The illustrative embodiments provide an apparatus for proper arm positioning and care of a patient on an operating room table. The arm positioning system improves arm and torso positioning, improves capability regarding patients that may have broader or wider arms and/or torso. The illustrative embodiments permit faster positioning of patient arm(s) and torso, enhanced safety features, and improved disposability for convenience. The illustrative embodiments also improve care of overweight, obese, and massively obese patients. Moreover, the embodiments describing disposable arm positioning apparatus provides easy disposability, improves cleanliness, and avoids cross contamination.

Frequently, a large patient's arm may be wholly or partially hanging over the edge of the operating table, which interferes with optimal operative exposure and access to the patient by medical personnel. The arm positioning system enables positioning and securing of the upper extremities so that medical personnel, such as a surgeon, may assume a desired position relative to the patient more easily. The arm positioning sleeve and body straps of the illustrative embodiments allows the arm to be moved into a position least likely to interfere.

The flowchart and block diagrams in the figures illustrate the architecture, functionality, and operation of possible implementations of methods, apparatus, and systems according to various illustrative embodiments. In this regard, each block in the flowchart or block diagrams may represent a step or instructions for implementing an embodiment(s). It should also be noted that, in some alternative implementations, the steps may occur out of the order noted in the figures. For example, two steps shown in succession may, in fact, be executed substantially concurrently, or the steps may sometimes be executed in the reverse order, depending upon the functionality involved.

The description of the present invention has been presented for purposes of illustration and description, and is not intended to be exhaustive or limited to the invention in the form(s) disclosed. Many modifications and variations will be apparent to those of ordinary skill in the art. The embodiments were described in order to best explain the principles of the invention, the practical application, and to enable others of ordinary skill in the art to understand the invention for various embodiments with various modifications as are suited to the particular use contemplated.

What is claimed is:

1. An arm positioning sleeve comprising:
   an inner surface adapted to be partially in contact with an arm of a user when in use during a medical procedure, wherein the user is a patient lying on an operating table and undergoing the medical procedure;
   an outer surface;
   a first end opposite to a second end;
   a first length of the first end of the arm positioning sleeve;
   a second length of the second end of the arm positioning sleeve, wherein the first length of the first end of the arm positioning sleeve is greater than the second length of the second end of the arm positioning sleeve;
   a first longitudinal side opposite to a second longitudinal side, wherein the first longitudinal side and the second longitudinal side are tapering from the first end to the second end to conform to a shape of the arm;
   an arm sleeve fastener, the arm sleeve fastener comprising a set of hook-and-loop fastener material strips on the inner surface along the first longitudinal side, the arm sleeve fastener further comprising a set of opposing hook-and-loop material strips on the outer surface, wherein the arm positioning sleeve is adapted to wrap around a portion of the arm of the user, and wherein the set of hook-and-loop fastener material strips on the inner surface are fastened to the set of opposing hook-and-loop material strips on the outer surface adapted to secure the arm positioning sleeve around the portion of the arm of the user; and
   an arm positioning sleeve to body strap fastener, the arm positioning sleeve to body strap fastener comprising a set of opposing hook-and-loop material strips on a portion of the outer surface of the arm positioning sleeve, wherein the set of opposing hook-and-loop material strips are fastened to hook-and-loop fastener material on an inner surface of a set of body straps, wherein fastening at least one body strap in the set of body straps to the set of arm positioning sleeves is adapted to secure each arm of the user lying on the operating table in a desired position for a remainder of the medical procedure.

2. The arm positioning sleeve of claim 1 wherein the arm sleeve fastener further comprises:
   a first length of at least one hook-and-loop fastener material strip in the set of hook-and-loop fastener material strips on the inner surface, wherein the at least one hook-and-loop fastener material strip is located along the first longitudinal side of the arm positioning sleeve, wherein the first length is within a range of six to twenty-four inches;
   a first width of the at least one hook-and-loop fastener material strip in the set of hook-and-loop fastener material strips on the inner surface of the arm positioning sleeve, wherein the first width is within a range from one inch to six inches;
   a second length of at least one opposing hook-and-loop material strip in the set of opposing hook-and-loop material strips on the outer surface of the arm positioning sleeve, wherein the at least one hook-and-loop material strip is along the second longitudinal side of the outer surface of the arm positioning sleeve, and wherein the second length is within a range of six inches to twenty-four inches; and
   a second width of the at least one opposing hook-and-loop material strip in the set of opposing hook-and-loop material strips on the outer surface of the arm positioning sleeve, wherein the second width is within a range from one inch to six inches.

3. The arm positioning sleeve of claim 1 further comprising:
   a length of at least one hook-and-loop fastener material strip on the inner surface of the arm positioning sleeve and located along the first longitudinal side of the arm positioning sleeve, wherein the length is seventeen inches long; and
   a width of the at least one hook-and-loop fastener material strip on the inner surface of the arm positioning sleeve and located along the first longitudinal side of the arm positioning sleeve, wherein the width is two inches long.

4. The arm positioning sleeve of claim 1 wherein the set of opposing hook-and-loop material strips on the portion of the outer surface of the arm positioning sleeve covers substantially all of a front side of the outer surface of the arm positioning sleeve.

5. The arm positioning sleeve of claim 1 further comprising:
   a padding on the inner surface of the arm positioning sleeve where the inner surface contacts the user.

6. The arm positioning sleeve of claim 1 wherein the arm positioning sleeve is disposable.

7. The arm positioning sleeve of claim 1 wherein the arm positioning sleeve is adapted to wrap around the portion of the arm of the user from a wrist of the user to a point on the arm above an elbow of the user.

8. A system for positioning a patient, the system comprising:
   an operating table;
   a set of arm positioning sleeves, wherein each arm positioning sleeve in the set of arm positioning sleeves is adapted to be wrapped around a portion of an arm of a user lying on the operating table, wherein the user is the patient undergoing a medical procedure, wherein the medical procedure is a surgery or operation, and wherein the set of arm positioning sleeves further comprises:
      a first longitudinal side of the each arm positioning sleeve;
      a second longitudinal side of the each arm positioning sleeve;
      a first length of a first end of the each arm positioning sleeve; and
      a second length of a second end of the each arm positioning sleeve, wherein the first length of the first end of the each arm positioning sleeve is greater than the second length of the second end of the each arm positioning sleeve, and wherein the first longitudinal side and the second longitudinal side are tapering from the first end to the second end to conform to a shape of a human arm;
   a set of body straps, wherein each body strap in the set of body straps is affixed to a side of the operating table at one end of the each body strap, and wherein the set of body straps further comprises:
      a first body strap connected to a first point of attachment on a first side of the operating table;

a second body strap connected to a second point of attachment on a second side of the operating table, a body strap to body strap fastener, the body strap to body strap fastener comprising a set of hook-and-loop body strap fastener material strips on an outer surface of the first body strap and a set of opposing hook-and-loop body strap material strips on an inner surface of the second body strap; wherein the each body strap in the set of body straps is adapted to be rotated over a torso of the user, and wherein the set of opposing hook-and-loop body strap material strips on the inner surface of the second body strap is fastened to the set of hook-and-loop body strap fastener material strips on the outer surface of the first body strap to secure the first body strap to the second body strap; and a set of arm positioning sleeve to body strap fasteners to fasten the set of arm positioning sleeves to the at least one body strap in the set of body straps, the set of arm positioning sleeve to body strap fasteners comprising: a set of hook-and-loop fastener material strips attached to an inner surface of the each body strap in the set of body straps;and a set of opposing hook-and-loop material strips attached to a portion of an outer surface of the each arm positioning sleeve in the set of arm positioning sleeves, wherein the set of opposing hook-and-loop material strips attached to the portion of the outer surface of the each arm positioning sleeve fastens to the set of hook-and-loop fastener material strips on the set of body straps, wherein fastening at least one body strap in the set of body straps to the set of arm positioning sleeves is adapted to secure each arm of the user lying on the operating table in a desired position at each side of the user for a remainder of the medical procedure.

9. The system of claim 8 further comprising:

an arm sleeve fastener attached to the each arm positioning sleeve in the set of arm positioning sleeves, the arm sleeve fastener comprising a set of hook-and-loop fastener material strips on an inner surface of the each arm positioning sleeve and a set of opposing hook-and-loop material strips on an outer surface of the each arm positioning sleeve, wherein the each arm positioning sleeve is adapted to be wrapped around the portion of the arm of the user, and wherein the set of hook-and-loop fastener material strips on the inner surface of the each arm positioning sleeve is fastened to the set of opposing hook-and-loop material strips on the outer surface of the each arm positioning sleeve adapted to secure the arm positioning sleeve around the portion of the arm of the user.

10. The system of claim 8 further comprising:

a width of the each body strap in the set of body straps, wherein the width is within a range of one inch to six inches wide; and a length of the each body strap in the set of body straps, wherein the length is within a range from twelve inches to forty-eight inches 11. The system of claim 8 wherein the set of body straps and the set of arm positioning sleeves are disposable.

12. The system of claim 8 wherein at least one body strap in the set of body straps is slidably affixed to a given side of the operating table and further comprising:

an end of the at least one body strap in the set of body straps slidably affixed to the given side of the operating table, wherein a location on the operating table at which the end of the at least one body strap is affixed to the given side of the operating table is adjustable, wherein the at least one body strap moves to the left or right along the given side of the operating table by the end of the at least one body strap slidably affixed to the operating table.

13. The system of claim 8 wherein the set of opposing hook-and-loop material strips on the portion of the outer surface of the set of arm positioning sleeves covers substantially all of a front side of the outer surface of the each arm positioning sleeve.

14. The system of claim 8 further comprising:

a padding on the inner surface of the each arm positioning sleeve where the inner surface contacts the user.

15. The system of claim 8 further comprising:

a width of the first body strap in the set of body straps, wherein the width is about three inches wide; and a length of the first body strap in the set of body straps, wherein the length is about thirty inches long.

16. A method for positioning a patient, the method comprising:

wrapping an arm positioning sleeve around a portion of an arm of a user lying on an operating table, wherein the user is a patient undergoing a medical procedure, and wherein the arm positioning sleeve comprises an outer surface and an inner surface;

fastening a set of arm positioning sleeve fasteners on the arm positioning sleeve to secure the arm positioning sleeve around the portion of the arm of the user, wherein a first length of a first end of the arm positioning sleeve is greater than a second length of a second end of the arm positioning sleeve, and wherein a first longitudinal side and a second longitudinal side are tapering from the first end to the second end to conform to a shape of the arm;

placing the arm of the user wrapped in the arm positioning sleeve in a desired position at a side of the user;

rotating a set of body straps over a torso of the user, wherein each body strap in the set of body straps comprises an outer surface and an inner surface, wherein the inner surface of the each body strap in the set of body straps comprises a set of hook-and-loop fastener material strips, and wherein the outer surface of the arm positioning sleeve comprises a set of opposing hook-and-loop material strips capable of fastening to the set of hook-and-loop fastener material strips; and fastening an arm positioning sleeve to body strap fastener to secure the arm of the user in the desired position for a remainder of the medical procedure, wherein the arm positioning sleeve to body strap fastener comprises the set of opposing hook-and-loop material strips on the outer surface of the arm positioning sleeve and the set of hook-and-loop fastener material strips on the inner surface of each body strap in the set of body straps.

17. The method of claim 16 wherein of a first body strap in the set of body straps is affixed to a right side of the operating table at one end of the first body strap, wherein a second body strap in the set of body straps is affixed to a left side of the operating table at one end of the second body strap wherein rotating the set of body straps over the torso of the user further comprises:

rotating the first body strap connected to the right side of the operating table over the torso of the user;

rotating the second body strap connected to the left side of the operating table over the torso of the user;

fastening a body strap to body strap fastener, wherein the body strap to body strap fastener comprises a set of hook-and-loop body strap fastener material strips on an outer surface of the first body strap and a set opposing hook-and-loop material strips on an inner surface of the second body strap, wherein the set of opposing hook-and-loop material strips on the inner surface of the second body strap is fastened to the set of hook-and-loop fastener material strips on the outer surface of the first body strap to secure the first body strap to the second body strap.

18. The method of claim 16 further comprising:

disposing of the arm positioning sleeve and the set of body straps after a single use.

19. The method of claim 16 wherein an end of each body strap in the set of body straps is slidably affixed to a side of the operating table, wherein a location at which the end of the each body strap is affixed to the side of the operating table is adjustable and further comprising:

sliding at least one body strap in the set of body straps along the side of the operating table to a desired position, wherein the at least one body strap moves to the left or right along the side of the operating table by the end of the at least one body strap slidably affixed to the operating table.

* * * * *